US007274443B2

(12) United States Patent
Ponstingl et al.

(10) Patent No.: US 7,274,443 B2
(45) Date of Patent: Sep. 25, 2007

(54) CORROSION MONITORING SYSTEM, OPTICAL CORROSION PROBE, AND METHODS OF USE

(75) Inventors: Michael Ponstingl, St. Louis, MO (US); Jess V. Ford, Arnold, MO (US); Anthony Johnson, St. Louis, MO (US)

(73) Assignee: Custom Sensors and Technology, Fenton, MO (US)

( * ) Notice: Subject to any disclaimer, the term of this patent is extended or adjusted under 35 U.S.C. 154(b) by 423 days.

(21) Appl. No.: 11/009,291

(22) Filed: Dec. 10, 2004

(65) Prior Publication Data

US 2005/0135546 A1    Jun. 23, 2005

Related U.S. Application Data

(60) Provisional application No. 60/528,379, filed on Dec. 10, 2003.

(51) Int. Cl.
*G01N 21/00* (2006.01)
(52) U.S. Cl. ............... 356/237.2; 356/300; 356/445; 250/341.1; 250/339.08
(58) Field of Classification Search ........... 356/237.2, 356/445, 317–319; 250/341.1, 339.12, 373, 250/341.6, 339.07, 339.08
See application file for complete search history.

(56) References Cited

U.S. PATENT DOCUMENTS

| | | | |
|---|---|---|---|
| 4,637,730 A | 1/1987 | Ponstingl et al. | |
| 5,045,703 A * | 9/1991 | Wieboldt et al. | 250/352 |
| 5,241,368 A | 8/1993 | Ponstingl et al. | |
| 5,327,225 A * | 7/1994 | Bender et al. | 356/445 |
| 5,332,900 A * | 7/1994 | Witzke et al. | 250/341.1 |
| 5,396,325 A | 3/1995 | Carome et al. | |
| 5,408,313 A | 4/1995 | Ponstingl et al. | |
| 5,519,330 A * | 5/1996 | Yamauchi et al. | 324/700 |
| 5,623,341 A * | 4/1997 | Hunt | 356/300 |
| 5,647,030 A * | 7/1997 | Jorgenson et al. | 385/12 |
| 5,745,243 A * | 4/1998 | Wilcox et al. | 356/419 |
| 5,793,042 A * | 8/1998 | Quick | 250/339.08 |
| 6,467,340 B1 | 10/2002 | Gallagher et al. | |
| 6,588,266 B2 | 7/2003 | Tubel et al. | |
| 6,678,050 B2 * | 1/2004 | Pope et al. | 356/435 |
| 6,792,357 B2 | 9/2004 | Menon et al. | |
| 2003/0071988 A1 | 4/2003 | Smith et al. | |

OTHER PUBLICATIONS

Philip-Chandy, R., Scully, P.J., and Thomas, D. "A novel technique for on-line measurement of scaling using a multimode optical fibre sensor for industrial applications." Sensors and Actuators B 71 (2000) 19-23. John Moores U.

* cited by examiner

Primary Examiner—Sang H. Nguyen
(74) Attorney, Agent, or Firm—Lewis, Rice & Fingersh, L.C.

(57) ABSTRACT

Optical corrosion monitoring and detection systems as well as methods to detect and monitor corrosion under process conditions and generally in real time using electromagnetic radiation, particularly light. The systems generally provide for incident light to be allowed to reflect from a coating which is exposed to the corroding action of the process stream. As the coating is corroded, the intensity, or other function, of the incident light is changed and this change is detected and used to extrapolate a level of corrosion.

22 Claims, 8 Drawing Sheets

CORROSION MONITORING SYSTEM, OPTICAL CORROSION PROBE, AND METHODS OF USE

CROSS REFERENCE TO RELATED APPLICATION(S)

This application claims priority to U.S. Provisional Patent Application Ser. No. 60/528,379 filed Dec. 10, 2003, the entire disclosure of which is herein incorporated by reference.

BACKGROUND OF THE INVENTION (1) Field of the Invention

The present invention pertains to probes for monitoring corrosion. Particularly for monitoring corrosion within pipes or tanks by utilizing electromagnetic radiation such as light.

(2) Background of the Invention

Corrosion presents a very real problem in systems which store, use, or transport corrosive materials. It is particularly important in piping or storage systems where corrosive materials, such as liquids or gases being stored or transported, may be in contact with the interior surface of a pipe or tank for an extended period of time, and where damage from corrosion may not be readily visible. If ignored, corrosion can eventually damage the piping or tank to a point where leaks or failures occur resulting in significant repair costs and possible other dangers.

While corrosion can occur in any type of piping or tank, it is particularly problematic in underground, undersea, or other difficult to access areas. Pipes susceptible to corrosion can be carrying crude oil, water, steam, or any other fluids or gases which are known to be corrosive to the metals of which piping is usually constructed. These pipes can also be corroded by the materials (such as water or earth) that they are placed within. Further, failure of these pipes can result in danger to occupants of buildings, can result in contamination of groundwater or similar resources, or can cause environmental damage.

Two methods are typically used to reduce and/or control corrosion in piping and storage systems: The first of these is passivity of the material surfaces. This type of control generally is used in the selection of materials for the piping or which coat the piping. These materials are generally chosen to be relatively inert compared to the fluids housed thereby and any surrounding materials. While this type of control can be effective, it is often very expensive. Further, coatings will often mechanically wear in a flow or may develop cracks over time which can lead to failure. Further, there are relatively few materials which are able to resist the wide variety of potentially reactive materials which may be in a process stream.

Because material selection is necessarily imperfect and quite expensive, the most common method for attempting to control corrosion is through the addition of corrosion inhibiting or control chemicals to the process stream which is within the pipe or tank. This method also is quite expensive due to maintenance down cycles and the ongoing costs associated with the required chemicals. Further, the method can actually create additional problems as the corrosion inhibiting chemicals may need to later be filtered out and may prove damaging to other systems which come into contact with the process stream. This method, however, often provides for controlled levels of inhibition at reasonable cost.

In many respects, corrosion control is not really the activity of trying to prevent corrosion outright, its simply trying to inhibit corrosion as much as possible so as to allow for piping and other products to have the longest possible useful life. Therefore, that corrosion occurs is often inevitable, the desire is simply to understand how much corrosion is occurring, attempting to reduce this amount of corrosion in a cost effective way, and being able to estimate and plan for maintenance and replacement costs.

It is well recognized that knowledge of the corrosion process that is occurring in the tank or pipe can help alleviate or reduce the continuing costs of unnecessary maintenance cycles and provide more cost effective use of chemical additives or passive materials. In the simplest sense, most process fluids will be comprised of a myriad of materials which may change over time. Therefore, the ability to actively monitor what corrosion is occurring provides for the most effective ability to react to these changes. Additionally, monitoring allows the operator to schedule maintenance as required due to actual system performance instead of on a fixed schedule, which may not be sufficient to eliminate failures or which may be overly conservative and, therefore, not cost effective. Therefore, an important component of corrosion resistance is detection of the type and rate of corrosion occurrence. With accurate detection, preventative strategies, such as inhibiting chemicals, can be added more efficiently.

Characterization of the corrosion process is preferred in the current production environment in order to meet increased requirements for profitability, worker safety, and environmental responsibility. Further, it provides for an improved ability to correctly react to a change in corrosion characteristics. With accurate determinations of corrosion, minimum amounts of chemical additives useful to hinder that type of corrosion may be added to the process streams.

It is well recognized that the most effective strategies for corrosion monitoring are placed within the pipe or tank so as to interact directly with the process stream. While external monitoring systems can be used, these systems often lack the sensitivity of systems placed in direct contact with the corrosion causing materials. Further, systems within a piping system or tank can more easily measure corrosion occurring in fairly static arrangements, such as a pipe system where water is maintained in a steady pressurized state as opposed to flowing.

The most prevalent monitoring method currently used is a coupon test system, where various coupons (typically materials used in the construction of the piping or storage system or which are particularly good indicators of corrosion) are placed within the system and exposed to the process stream. These coupons then corrode, or show effects indicative of corrosion, in a manner which allows extrapolation of the corrosion within the entire piping or storage system. While this method works reasonably well, it often requires draining of the piping or storage system to remove the coupon for inspection and analysis. Furthermore, coupons can be difficult to use in inaccessible locations such as underwater, underground, or in dangerous environments as they are not easily retrieved. Coupons also are not necessarily exposed to the same forces as the pipe walls due to required positioning. Coupons also cannot give real time determinations of the corrosion within the piping or storage system, so conditions can only be determined during scheduled maintenance periods, when the coupons can be removed or analyzed. This means an unexpected problem can develop within the maintenance interval without warning. Further, these systems are not very reactive to sudden changes.

There have been designs proposed for real time corrosion probes which measure electrical properties of the process stream, or which are able to measure various other properties of the process stream directly. The problem with these systems is that many process streams do not conduct electricity rendering the first type of probes unusable for these applications. Secondly, often a particular characteristic of a process stream can provide nothing more than an educated guess as to how mush corrosion is actually occurring. In these situations, a large amount of data may need to be collected and analyzed for the determination, and even large collection systems may not take into account every factor that needs to be examined to accurately measure corrosion. Further, many corrosive process streams are also corrosive to probes or measurement devices in the probes resulting in their destruction over time. This can lead to frequent replacement of expensive probes and increases the possibility of probe malfunction due to damage.

SUMMARY OF THE INVENTION

To deal with these and other problems in the art, described herein are optical corrosion monitoring and detection systems as well as methods to detect and monitor corrosion under process conditions in real time using electromagnetic radiation, particularly light. That is, a corrosion monitoring system such as those described herein can measure (or more accurately approximate or extrapolate) the level of corrosion occurring in a piping or storage system without having to drain the entire system and at any given instant in time. The extrapolation is generally performed by providing a particular amount of a coating on a substrate, and determining the amount of the coating which has corroded away based on changes in the reflectance of light off the coating.

In an embodiment, there is described herein, a corrosion monitoring system comprising: a source of electromagnetic radiation; a detector of electromagnetic radiation; and a window comprising: an optical substrate; and a coating; wherein, the coating is placed in contact with a process stream that causes the coating to corrode over time; wherein, the source emits electromagnetic radiation into the optical substrate; wherein the electromagnetic radiation at least partially reflects from the coating; wherein the detector detects the electromagnetic radiation reflected from the coating; and wherein a level of corrosion of the coating can be extrapolated from the output of the detector.

In an embodiment of the corrosion monitoring system the optical substrate is selected from the group consisting of: sapphire, quartz, silica, glass, and plastic.

In an embodiment of the corrosion monitoring system the coating may comprises material used in a vessel, such as, but not limited to, a tank or piping, housing the process stream.

In an embodiment of the corrosion monitoring system the window is mounted in a probe and the source and the detector are in a processing system located remote from the probe. In an embodiment the processing system and probe are connected via at least one fiber optic cable.

In a embodiment of the corrosion monitoring system the process stream may include crude oil, water, or materials suspended therein.

In an embodiment of the corrosion monitoring system the electromagnetic radiation may comprise visible light, ultraviolet (UV) light, or infrared (IR) light.

In another embodiment, there is described herein, a corrosion monitoring system comprising: an original intensity of electromagnetic radiation; and a window comprising: an optical substrate; and a coating which includes a material and a product of the material created by corrosion; wherein, the original intensity of electromagnetic radiation is incident to the coating, the coating reflecting a lower intensity of the electromagnetic radiation; and wherein the ratio of the lower intensity to the original intensity is related to the ratio of the material to the product of the material created by corrosion.

In yet another embodiment of the corrosion monitoring system the electromagnetic radiation comprises visible light, ultraviolet (UV) light, or infrared (IR) light.

In a still further embodiment, there is described herein, a method for extrapolating the corrosion caused by a process stream, the method comprising: providing a probe including a window, the window including an optical substrate with a coating thereon; placing the probe in a manner such that the coating is in the process stream; illuminating the coating with an intensity of electromagnetic radiation, such that a first reflected intensity of electromagnetic radiation is reflected by the coating; allowing the coating to be corroded by the process stream to create a corroded coating; illuminating the corroded coating with an intensity of electromagnetic radiation, such that a second reflected intensity of electromagnetic radiation is reflected by the coating; comparing the first reflected intensity to the second reflected intensity; and extrapolating from the comparison the corrosion caused by the process stream.

In a still further embodiment of the method the intensity of electromagnetic radiation is the same in both the steps of illuminating and may comprise visible light, ultraviolet (UV) light, or infrared (IR) light.

BRIEF DESCRIPTION OF THE DRAWINGS

FIG. 3 provides multiple cutaway views of an embodiment of an optical corrosion probe.

DETAILED DESCRIPTION OF THE PREFERRED EMBODIMENTS

In a general overview, an embodiment of the corrosion monitoring system preferably operates on the concept of reflectance from a surface. The embodiments discussed herein presume that the corrosion causing material is a fluid and that the fluid is within a section of pipe whether in a stationary or flowing state. For ease of description, the system encasing the process stream will often be referred to as a pipe, however, this term is not intended to be limiting to particular vessels for holding or transporting the process stream. The corrosion caused by the fluid's interaction with the material of the vessel is the corrosion which is desired to be monitored or detected. The fluid in the vessel being monitored is referred to as a process stream. The term "process stream" is used because in most situations that fluid will be flowing or moving in the pipe. However, the term is in no way intended to require that the fluid be moving. Further, while the stream will generally be presumed to be a fluid or liquid, this description is not intended to be limiting and one of ordinary skill in the art would understand that the systems and methods disclosed herein could be used for any corroding material (whether in liquid, gaseous or other state) located in any type of vessel to monitor any type of corrosion caused thereby. The corrosion monitoring systems discussed herein can be used if the corrosive effect is caused by the process stream, or by items suspended or in solution with the process stream, or by the interaction of the process stream with any material also present in the system and the structure of the vessel. These situations will still however be referred to as corrosion by the process stream as the process stream is intended to refer to any material(s) inside the vessel.

Figure 1:
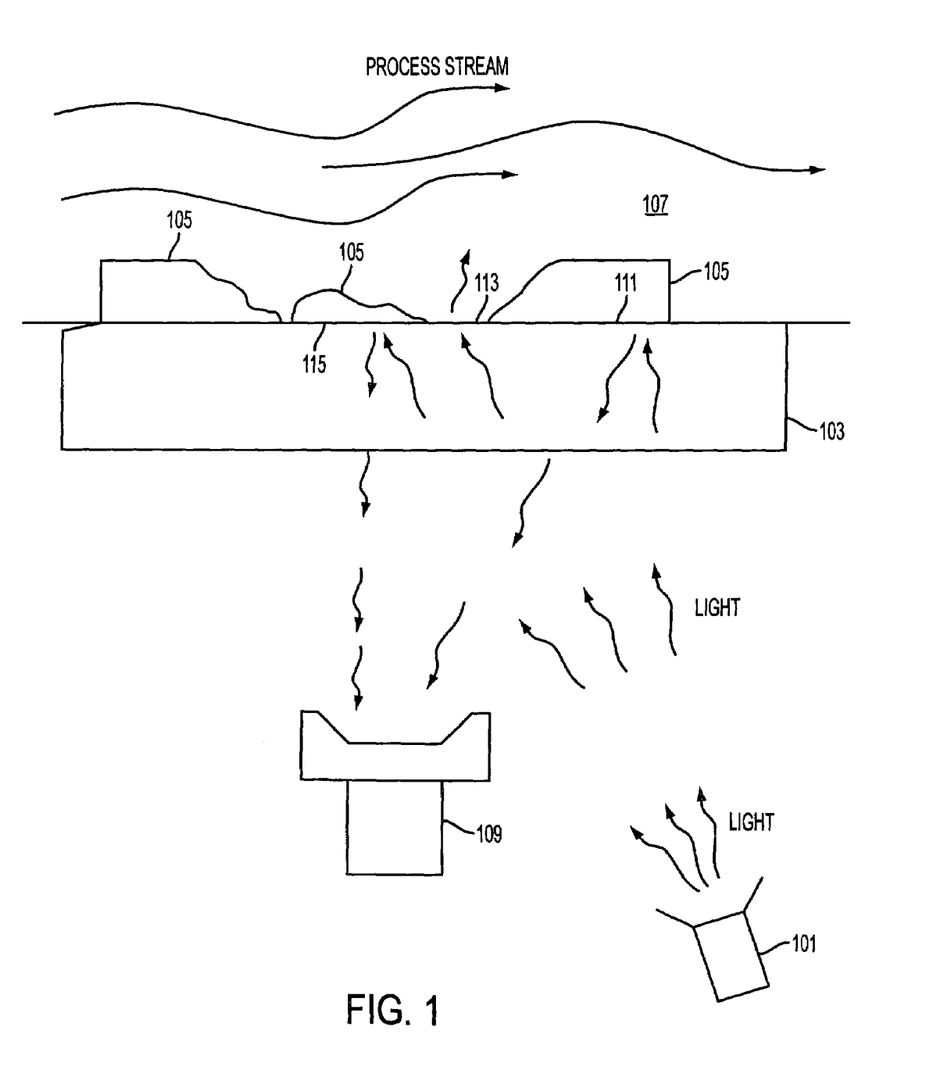
FIG. 1 shows an embodiment of reflectance from a partially corroded probe window.

A simple diagram of an embodiment of the optical measurement mechanism for detecting a change in reflectance due to the occurrence of corrosion is illustrated in FIG. 1. FIG. 1 is intended to be illustrative of concepts and is therefore fairly exaggerated. Generally, light from a stable light source (101) passes through an optical substrate (103) and impinges on a coating (105) which is on the exterior of the optical substrate (103) and in contact with the process stream (107). The coating (105) is reflective to the impinging light and the reflected light (the reflectance) from the coating (105) is directed into a collector (109). Without the coating (105) having experienced any type of corrosion, a fixed percentage of the light intensity inbound on the coating (105) will be reflected (often very close to 100%).

As the coating (105) is however exposed to the process stream (107), the coating (105) is corroded by its contact with the process stream (107). As corrosion caused by the process stream (107) occurs, the coating (105) thickness and/or reflectivity at a given point will generally change, from the change in reflectivity, the corrosion in the vessel as a whole can be extrapolated. In particular, corrosion will generally cause molecules of the coating (105) to be chemically altered. This alteration may change the reflectivity of the molecule, may alter the structure of the molecule in the coating (105) changing the reflectivity of the coating (105), or may weaken the molecules binding strength with the rest of the coating (105) allowing it to more easily be mechanically eroded. Regardless of which type of change occurs, the reflectivity of the coating (105) will generally change slightly.

The alteration in reflectance is demonstrated by examining points (111), (113), and (115) on FIG. 1 where loss of material is used as indicative of corrosion. At point (111) the coating (105) is still its full original thickness having experienced no corrosion directly. At point (113) the portion of the coating (105) has been entirely corroded away, leaving a space where there is no coating (105). At point (115), the coating (105) is thinner than it was having experienced some corrosion. This type of arrangement is fairly indicative of the way corrosion actually occurs. A surface will not corrode uniformly at a small scale, but will have sections with little to no corrosion, and others which are heavily corroded. The existence of different areas and the prevalence of them will effect the reflectivity of the substance.

Light (or other electromagnetic radiation although light as used herein is intended to mean any form of electromagnetic radiation) incident on the coating (105) impacts a measurable area sufficiently large so that corrosion of a single molecule of coating (105) does not result in a change to all incident light. The exact size of this area of incidence depends on the desired design of the probe but will generally be at least a few square millimeters. If there is no corrosion, the light will be reflected back at all points as the entire surface of the area has sufficient coating (105) to produce reflectance. This is the case where no corrosion (or minimal corrosion) has occurred. Once the material of the coating (105) has completely corroded away, there is no longer an interface between the coating (105) and the substrate (103). In this instance, the boundary between the process stream (107) and the optical substrate (103) will generally produce minimal reflectance as the light passes into the process stream (107).

As the coating (105) corrodes, the amount of light being reflected will therefore decrease until it has reached a minimum level of reflectance. This change will be the result in the corrosion of the different points (111), (113), and (115) and the prevalence of points of each type in the coating (105) as a whole. At the point (111), the coating (105) has not been corroded and remains at its original thickness. Therefore, light incident on the coating at point (111) is fully reflected. At point (113), the entire thickness of the coating (105) has been removed by the corrosion (it has corroded) or has been sufficiently thinned by corrosion that the light incident on that point is not reflected at all and instead passes into the process stream (107). At a point (115), the coating (105) has thinned. In this area, incident light may still be partially reflected. Alternatively, the light may be refracted and, while still being partially reflected, has most of the intensity scattered.

It is important to note that the points (111), (113) and (115) are, in practice, extraordinarily small. In particular, each individual photon from the light source, when reaching the coating (105), will determine its own path either missing the coating (105) and passing into the process stream (107), being reflected by the coating (105) to the light collector (109), or being refracted either into the collector (109) or away from the collector (109). As the surface of the coating (105) thins and becomes increasingly pitted from corrosion occurring, the reflectance intensity incident on the collector (109) decreases because more photons will not be reflected back to the collector (109) as they are either being refracted or passing into the process stream (107). The macro scale light intensity change can then be detected. This change can then be calibrated to the levels of corrosion occurring through experimental examination or mathematical calculation.

Therefore, the description of FIG. 1 shows a small portion of what is happening on a relatively large scale. As corrosion occurs in the coating (105), the bombardment of electromagnetic radiation will result in fewer and fewer individual photons being reflected back to the collector (109). This change will effectively result in a decrease in reflected light intensity detected by the collector (109). The total illumination intensity is not really changed, just more of that intensity is now not reflected back to the collector (109).

While the above presumes that the corrosion actually removes the coating (105) as it progresses, this is by no means required. In an alternative embodiment, a change of state of the coating (105) may also or alternatively be detected. For instance, if the coating (105) is iron, the conversion of the iron to iron oxide will generally alter the reflectivity of the coating (105), even without it actually being removed by the corrosion effect (or by erosion of weakened structure) leading to a similar change in intensity. However, the general phenomena is the same. Less of the original light is being reflected back to the light detector (109) so a decrease in light intensity is detected.

In an embodiment, the corrosion sensor preferably uses optical interface coupler technology, which is designed to handle the elevated temperatures and pressures of many industrial processing applications. Further, the electronics required to interrogate the optical signal also preferably operate in the production environment, although will not generally need to operate in the process stream (107), with a minimum of operator intervention. This provides for relatively continuous monitoring and a relatively low chance of major damage or error being incurred due to corrosive effects. An embodiment of such an arrangement is shown in FIGS. 2 and 3.

Figure 2:
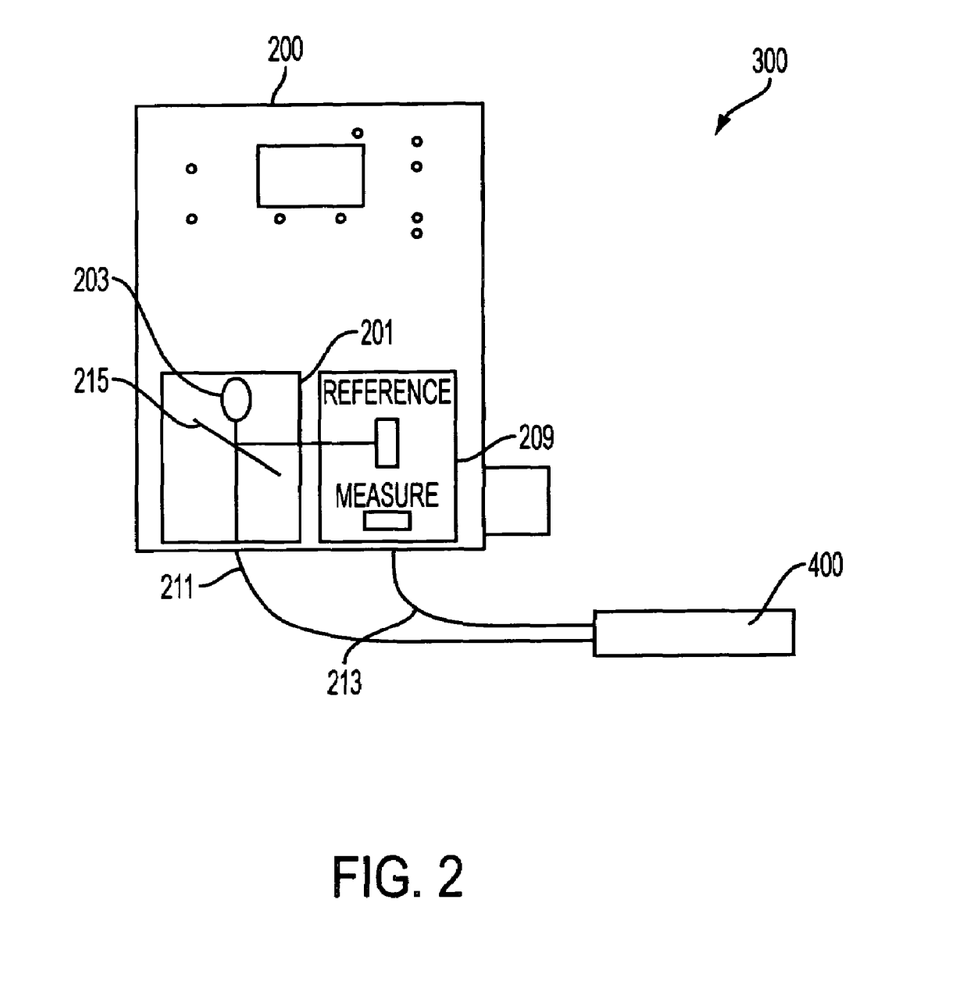
FIG. 2 provides a block diagram of an embodiment of a corrosion monitoring system.
Figures 3A, 3B, 3C, 3D:
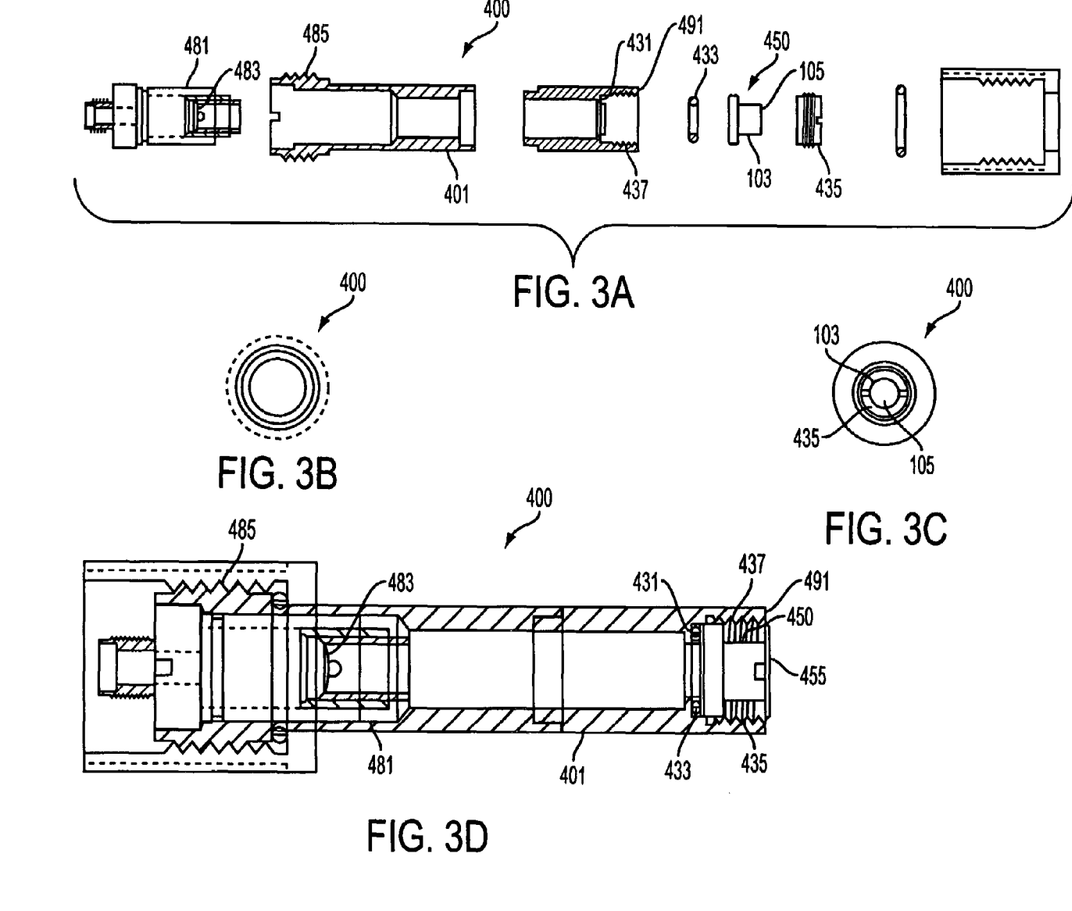
FIG. 3A is an exploded view.
FIGS. 3B and 3C are end views.
FIG. 3D is an assembled view.

The corrosion monitoring system (300) of FIGS. 2 and 3 comprises two major components: a corrosion monitoring probe (400) (shown generally in FIG. 2 and in detail in FIG. 3), and a processing system (200). While these systems are discussed herein, other technologies related to process application probes can be used instead of or in addition to those described herein. Some disclosures which can be used to provide detail of alternative probes include U.S. Pat. No. 5,408,313 and U.S. patent application Ser. No. 10/815,295 entitled "Fiber Optic Fluid Probe." The entire disclosure of both of these documents is herein incorporated by reference.

Examining FIG. 2, the processing system (200) generally comprises an optoelectronic device (201) that sends light from a source (203) into the monitoring probe (400). The source (203) is preferably, but is not limited to, a visible (VIS) or near infra-red (NIR) based light emitting diode (LED), a Tungsten Halogen Lamp, a xenon flash lamp covering the ultraviolet (UV) through NIR regions of the spectrum (200 nm to 2800 nm), or a combination of the above. In alternative embodiments, the source (203) may be any source of electromagnetic radiation capable of being reflected by the coating (105) and can include, but is not limited to, LEDs, Organic LEDs, filament based light sources, electric arc light sources, lasers, bioluminescent light sources, or sonioluminescent light sources. Further, while this disclosure uses the term "light" to describe the electromagnetic radiation, there is no need for the light to be visible light and may be ultraviolet light, infrared light, or any other form of electromagnetic radiation capable of reflection by the coating (105).

Two fiber optic cables (211) and (213) are provided to steer the light waves generated by the source (203) to or from the probe (400). Cable (211) steers the light from the source (203) toward the probe (400). Cable (213) directs reflected light from the probe (400) into at least one detector (209) which is capable of detecting the intensity of the light. In an alternative embodiment, a property of the light other than intensity (such as interference) may be used as would be understood by one of ordinary skill in the art, but this disclosure will focus on reflected light intensity being used as the corrosion indicator. Either or both of the fiber optic cables (211) and (213) may connect to an optical splitter (215) to provide a reference signal to the detector (209) or to provide part of the light signal for other use. In the depicted embodiment, the optical splitter (215) is simply a piece of material similar to optical substrate (105) arranged at an angle (generally about 45°) to the incident light beam. However, any optical splitter known to those versed in the art may be used to direct the light beam(s) to the required detectors and the system is in no way limited to mechanical or fiber optic arrangements. In an embodiment, the reference signal is provided so that the reflected intensity can be determined based on the actual light output. The processing system (200) can therefore make an accurate determination of the reflected light intensity even if the source light intensity includes small variations.

As shown in FIG. 2, the light source (203) and detector (209) are preferably located in the processing system (200) with the light being transmitted to and from the remote probe (400) using cables (211) and (213). In an alternative embodiment, the light source (203) and/or detector (209) may be located within the probe (400). In this alternative embodiment, the probe (400) would generally include some form of transmission means (such as a radio frequency (rf) transmitter) to transmit the output of the detector (209) from the probe (400) to the processing system (200). In a still further embodiment, the probe (400) may include any or all components of the processing system (200). It is generally preferred that the light source (203) and as many other systems as possible be in the optoelectronic device (201) and remote from the probe (400) as it makes the probe (400) less expensive to manufacture. As the probe (400) may be at least partially exposed to the process stream (107) and can become corroded or otherwise damaged over time, keeping the probe (400) more easily disposable is a desirable trait.

The processing system (200) may also include an output designed to interface with any type of monitoring or reaction system for use with the vessel and to allow for a more automated system. In such an arrangement, the output signal from the corrosion monitoring system (300) is preferably an industry standard signal such as, but not limited to, a 4-20 mA signal, which is compatible with all common process control and monitoring systems and allows for integration of the corrosion monitoring system (300) with other monitoring or control systems. The processing system (200) or these remote systems may then provide control for facets of the process stream, an alarm signal, or simply a monitor or detector for corrosion.

Figure 8:
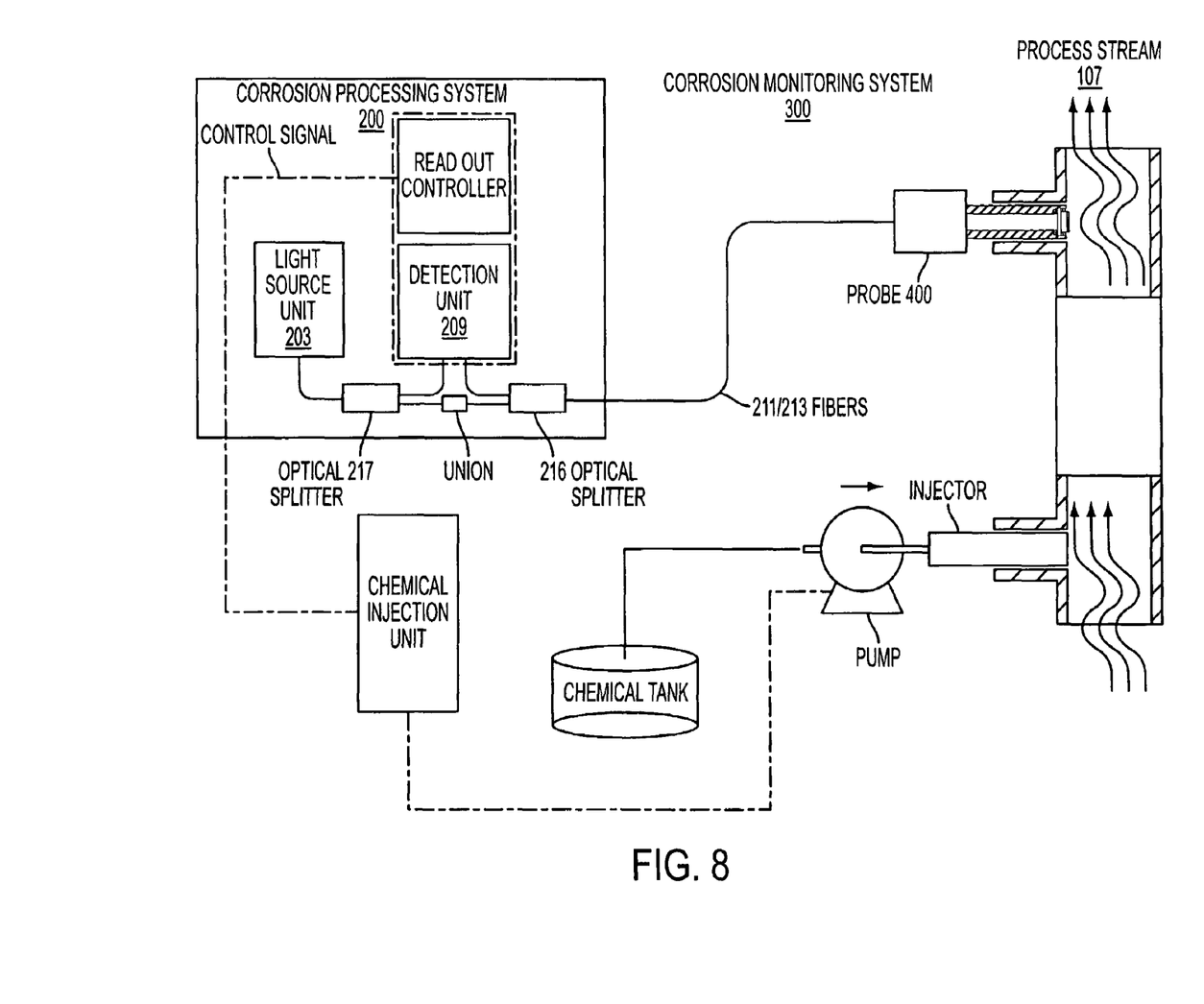
FIG. 8 provides a block diagram of an embodiment of a corrosion monitoring system including a system to control chemical output into the process stream.

When the corrosion monitoring system (300) is being used as part of a system to control output such as is shown in FIG. 8, a predetermined level of corrosion reducing chemicals can be introduced based on the level or rate of corrosion detected by the probe (400) at any given period or over any window of time. If the rate of the corrosion is detected to increase, or if simply more corrosion is occurring, the corrosion monitoring system (300) may increase the amount of chemicals being introduced to the process stream (107) to compensate. At the same time, if the total corrosion level is higher, the corrosion monitoring system (300) may signal for use of more chemicals to try and inhibit corrosion by an increased amount to prevent a possible failure.

Control processes can also provide for feedback in conjunction with the corrosion monitoring system (300). In particular, the probe (400) and optoelectronic device (200) together can indicate the effectiveness of various treatments. In particular, if a first level of corrosion is monitored with a particular level of chemicals, more chemicals can be added and the new level monitored. The control process can then determine an optimum level of chemicals to use based on various cost inputs provided by a user. Further, if the corrosion is found to increase over time with the same amount of chemicals, more chemicals can be added which should reduce the level back to an expected amount. If this does not occur, it may be indicative that the corrosion is being caused by something which is nonreactive to the chemicals being used or that there is a problem with the chemical feed system such that chemicals are not being fed correctly. These can result in other checks, or in the use of a different chemical mix to attempt to inhibit corrosion.

In an alarm signal situation, a particular level of occurred corrosion or a significant increase in corrosion can indicate a warning situation. In this situation, the alarm will signal to maintenance personnel, or to other systems, that there is a potential change or potential concern. This alarm can indicate corrosion inhibiting materials need to be introduced (or altered in their rate of introduction), preventative maintenance needs to be performed, or even that a failure has occurred elsewhere that has effected the process stream composition. The alarm could also trigger more drastic measures. In a particularly fragile environment (for instance where failure of a pipe could result in massive environmental damage), the alarm could trigger shutdown of related systems to prevent the possibility of damage, could reduce pressure in pressurized systems, or could evacuate the pipe. In this way a potential pipe rupture could be averted and the maintenance can be performed.

In a monitor or detector situation, the corrosion monitoring system (300) could simply provide an indication of the level of corrosion occurring as a numerical, percentage, or any other type of display which can be used by maintenance personnel to monitor the system and determine what steps may be desirable based on the corrosion occurring. The monitor or detector can also be used to simply provide data indicating when maintenance should be performed or to calculate when costs are likely to be incurred in the future to improve planning. For instance, a detector may be able to determine the rate at which pipes are corroding over time. From this rate, maintenance personnel may be able to schedule a window when maintenance should be performed. This window can take into account external factors in determining when to schedule maintenance or even replacement of the pipe. The cost of this maintenance can then be minimized (as there shouldn't be any need of emergency repair) and can be budgeted over time.

The corrosion probe (400) is shown in more detail in FIG. 3. In the depicted embodiment, the probe (400) comprises a body (401) for mounting the various components. It may also include an optical interface (481) for interaction and interface with the processing system (200). The optical interface (481) in the depicted embodiment comprises a hook up for the fiber optic cables (211) and (213) to the optical interface (481) and a lens (483) such as one to collimate or focus the energy to or from the window (450) to improve light intensity and focus on the window (450). The exterior of the body (401) may include a removable connector (485) such as screw threads for allowing removal of the probe (400) from a mounting in the pipe or tank.

The measuring of reflectance will generally occur using one or more windows (450) which comprise the target of the emitted light from source (203). In the depicted embodiment, the probe (400) includes only a single window (450), but one of ordinary skill in the art would understand how multiple windows (450) can be used in the same probe (400) simultaneously through the use of beam splitters, lenses or similar devices. Each window (450) comprises an optical substrate (103) with some coating (105) which is exposed to the process stream (107). It is preferred that a window (450) be removable from the probe (400) so as to be replaced when the coating (105) has corroded to the point that it is no longer useable to detect additional corrosion.

In the depicted embodiment of FIG. 3, the window (450) is designed for ease of removal. This is shown in the detail view of the window (450) in FIG. 4. In the depicted embodiment, the optical substrate (103) is shaped as a columnar section (441) with a flat terminus end (443) extending from a disk (445). This forms a shape generally similar to that of a top hat. The optical substrate (103) can be either hollow or solid based on reflectance and cost considerations. The top hat design is merely a preferred embodiment, and in other embodiments, the optical substrate (103) can be of any shape. The coating (105) is preferably placed on the terminus end (443) of the columnar section (441) but in an alternative embodiment can cover the entire surface of the columnar section (441). The top hat design improves light focus on the surface interface between the optical substrate (103) and the coating (105) where (or near where) reflection will occur.

Figure 4:
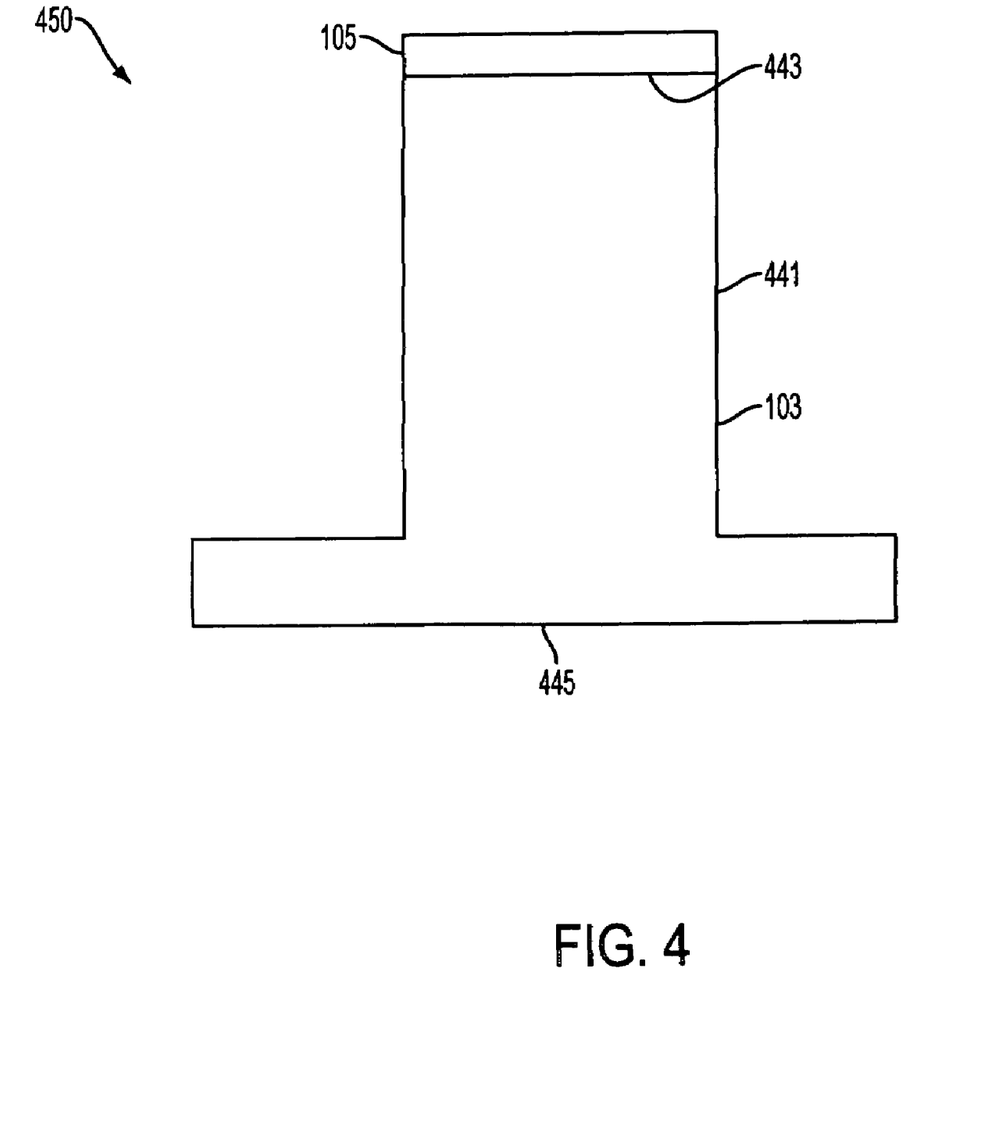
FIG. 4 provides a side view of an embodiment of an optical corrosion probe window.

The disk base (445) is generally used to removeably attach the window (450) to the body (401) of probe (400). The disk (445) is generally placed over an O-ring (433) and placed into the probe (400) against a shoulder (431) placed towards the distal end (491) of the interior of the probe (400). A mechanical retaining ring (435) is next inserted over the columnar section (441) and in contact with the disk (445). The mechanical retaining ring (435) is then is preferably screwed into internal threads (437) of the probe (400). The mechanical retaining ring (435) serves to press the disk (445) into the O-ring (433) which in turn is compressed into the shoulder (431) to provide a mechanical process seal.

To remove the window (450), the probe (400) is first removed from the process stream. Then, the mechanical retaining ring (435) is removed with a spanner wrench from the rest of the body (401). The expended window (450) is dropped or pulled out from the end of the probe (400) and a new window (450) is inserted onto the O-ring (433). The mechanical retaining ring (435) is then reinserted and tightened with the same spanner wrench to compress the window (450) into the retaining ring (435).

The O-ring (433) may serve several functions. In particular, the O-ring (433) may seal the surface of the window (450) to the body (401) of the probe (400) to prevent the process stream (107) from leaking into the probe (400). Further, the O-ring (433) can act to minimize galvanic differences between the optical substrate (450) and the probe body (401) which may introduce error into calculations or measurements.

The optical substrate (103) can comprise any material which is transparent (or of known translucency) to the generated light. The optical substrate (103) is essentially used as a support for the coating (105) and therefore allows transmission of the light whether impinging on the coating or reflecting therefrom. The optical substrate (103) may be particularly selected to provide for a high reflectivity from the interface of the optical substrate (103) and the coating (105) as is understood by those of ordinary skill in the art. Depending on the embodiment, the optical substrate (103) may comprise, but is not limited to, sapphire, quartz, silica, glass, plastic, or any other material or combination of materials capable of allowing transmission of at least a portion of the electromagnetic radiation incident thereon. The optical substrate (103) may also include pockets of air or other gases which allow for electromagnetic radiation transmission. While the term "optical" substrate is used to describe this material, the optical substrate (103) need not necessarily be transparent to visible light, only to at least some of the particular wavelengths of electromagnetic radiation being emitted from the source (203). The optical substrate (103), in an embodiment, may by translucent and allow only certain wavelength of the emitted light to pass therethrough. Such a system can provide for a very particular light to be impinging on the coating (105) which may be beneficial if such particular characteristics are useful in detection. In a still further embodiment, the optical substrate (103) can carry out other modifications on the light as it passes therethrough. For instance, the optical substrate (103) may polarize the light.

The body (401) of the probe (400) is preferably constructed of strong resilient materials and can be constructed of stainless steel (Such as, but not limited to, 304SS or 316SS), Hastelloy C-276, Monel, Carpenter 20, or any other metal or material that is compatible with placement in the process stream to be measured. Preferably, the material of the body (401) will be relatively non-reactive or minimally reactive with the process stream (107) and conditions of the process stream (107). The O-ring (433) material can be Buna-n, Teflon, Viton, Chemraz, Kalrez, or any compressible material compatible with, and preferably non-reactive or minimally reactive with, the process stream (107) and conditions of the process stream (107).

Generally, corrosion monitoring system (300) (particularly the optical probe window (450)) will be constructed and selected for use with a particular environment in order to improve detection accuracy. In particular, the coating (105) will preferably be selected to comprise the same material(s) as the vessel whose corrosion is to be monitored. However, this is not always possible in all types of piping as the material may not be reflective, may not allow for reflection from its proximity to the optical substrate (103), or may be ineffectively reflective. The material may also not be able to be practically deposited on the optical substrate (103) or may be unusable for any other reason.

In these situations, or if otherwise desired, the coating (105) may be selected to be reflective (or provide for reflection) and to have known corrosion statistics related to corrosion of materials of a vessel without being a material of which the vessel is constructed. This selection may take place based on both the material whose corrosion characteristics are to be extrapolated and the process stream (107) which is being used. Further, the type of corrosion may also be used in making this determination. Materials which have known relationships such that corrosion of one can be used to extrapolate corrosion of another are known to those of ordinary skill in the art or may be determined experimentally. In a still further embodiment, the material may be selected based on the process stream (107) being monitored and the expected cause of corrosion. In this way, the probe (400) may react more strongly to the fluid than a pipe will react to provide for finer control and a larger scale for the signal.

Each window (450) that is to be used in the probe (400) may be prepared in a similar or different manner. In an embodiment of the corrosion monitoring system (300), multiple probes (400), or a probe (400) having multiple windows (450), may be used in conjunction with each other. In such a system, the coating (105) of each window (450) may be different to provide for different corrosion monitoring mechanisms or may be similar to provide for double checking and to eliminate potential spot anomalies. In a preferred embodiment, the coating (105) placed on the optical substrate (103) is a metal (more preferably a metal used in piping) and may be prepared by, but is not limited to, a sputtering technique as is known to those of ordinary skill in the art.

Sputtering is a technique known to those of ordinary skill in the art and may be used as follows to create window (450). The optical substrate (103) is first placed in a vacuum chamber with a target of the material to be deposited. A plasma is generated in a passive source gas (i.e. Argon) in the chamber, and the ion bombardment is directed towards the target, causing material to be sputtered off the target and condense on the chamber walls and the optical substrate (103). A strong magnetic field (magnetron) can be used to concentrate the plasma near the target to increase the deposition rate. Other coating technologies known to those of ordinary skill in the art can also be used to fabricate the required sensing surface, with the exact deposition technology to be dictated by the coating (105) used.

The design of the coating (105) will generally depend on the intended measurement characteristics of the window (450). Depending on the type of material in the process stream (107), the type of corrosion to be measured, or the construction of the vessel, among other things, the coating (105) may be selected to provide for the desired type of measurement. In the depicted embodiments of FIGS. 5-7, various different geometric shapes for the coating (105) are shown. The exact dimensions of the geometric shapes may be selected based on the process stream (107) and the coating (105) material, amongst other things.

Three shapes which are used in different embodiments are flats, wedges, and cones. In alternative embodiments, where different corrosion characteristics are to be measured, other shapes may be used such as, but not limited to, cylinders, pyramids, nubs, toroids, hemispheres, (or related structures such as, but not limited to, hemiellipsoids or hemiparaboloids), wave patterns, or any other surface pattern. Further, in the depicted embodiments, these shapes are formed from a single type of material. In an alternative embodiment, different types of materials may be incorporated into the shapes as different layers, sections, portions, or as a mixture. A two component coating (105) can be used to represent a coated pipe for instance, where a protective coating is provided over a more corrosion sensitive material. Alternatively, the coating (105) could have two different materials where failure of either or both could pose a problem so that the system is monitoring both at once.

Figure 5:
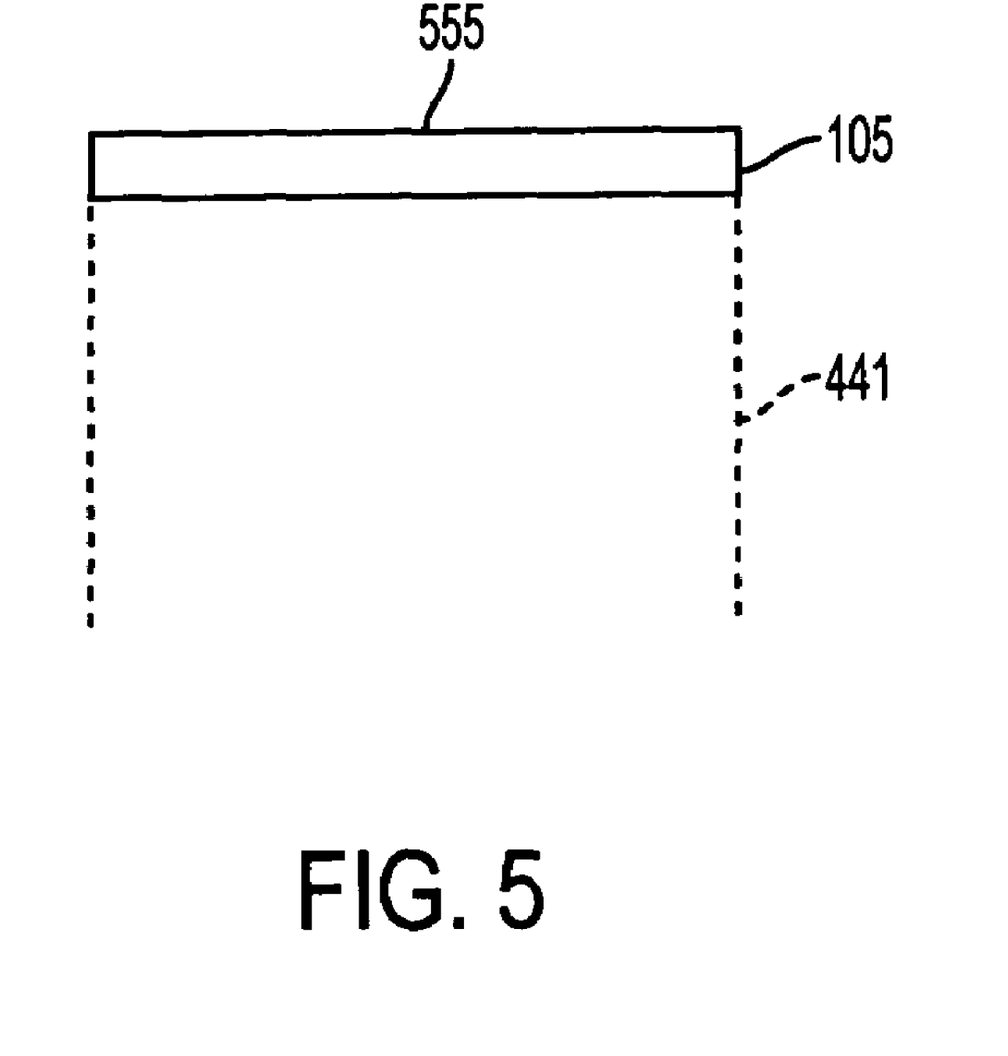
FIG. 5 provides a detail diagram showing an embodiment of an optical corrosion probe window with a flat coating.

A flat coating (555) is depicted in FIG. 5. A flat coating (555) would generally be the most common form of coating (105) as surfaces in piping will generally be flat. Further, because of the amount of surface area of the optical substrate compared to the volume of a flat coating (555), this would generally also be the most sensitive surface. In a flat coating (555), a relatively even thickness of coating material is placed onto the surface of the optical substrate (103) which will be used to generate reflectance. The general thickness of this type of approach is preferably relatively uniform and between 10 and 100 nm thick, but any thickness can be used as determined by monitoring goals and the particular corrosive nature of the process stream (107). The exact thickness will generally depending on the type of material used in the flat coating (555), and the type of detection which is to be performed. In a preferred embodiment, a flat coating (555) about 40 nm thick provides for rapid detection of corrosion occurrence.

Figure 6:
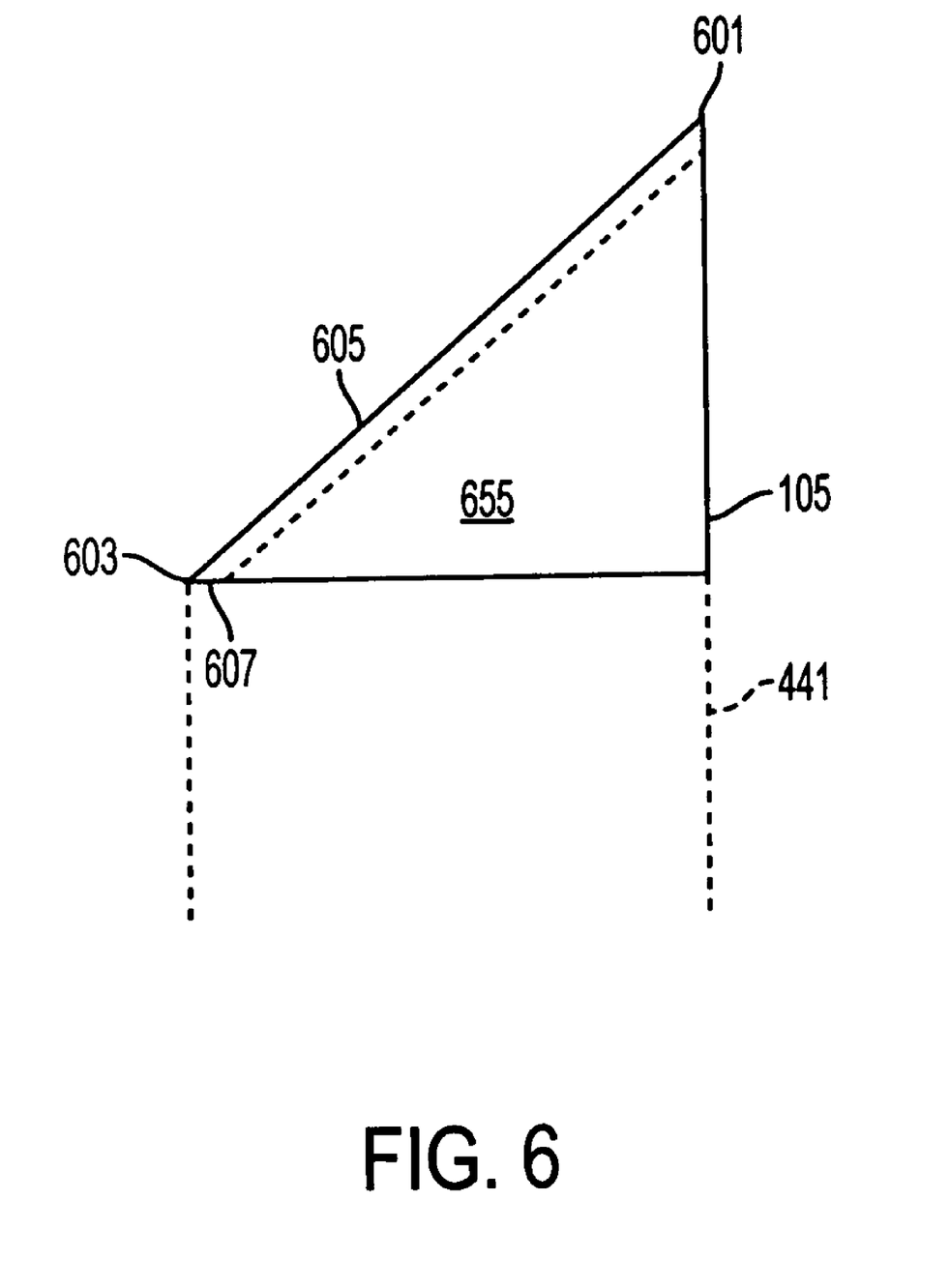
FIG. 6 provides a detail diagram showing an embodiment of an optical corrosion probe window with a wedge coating.

A wedge coating (655) is depicted in FIG. 6 and is a preferable shape when longer term monitoring is desired, when long term corrosion rate is desired to be controlled, and/or when the process stream (107) in which the probe (400) is immersed has a relatively high corrosion rate. The wedge coating (655) is thick on its first end (601) and tapers at a relatively constant angle to a very thin buildup on its second end (603). In a preferred embodiment, the wedge coating (655) at the first end (601) is about 3500 nm and tapers to about 0 nm at the second end (603). The sides and end of the wedge coating (655) will generally be shielded from corrosion in the process stream (107) such as, but not limited to, by other structures or by selected placement. As the wedge coating (655) corrodes, the thinnest section will rapidly disappear, while the thicker section takes much longer to shrink to a width where light is allowed to escape (even though it should corrode at relatively the same rate in the macro scale). Effectively, a layer of the face (605) will be removed over a particular period of time on the wedge design. The change in the removal of this face (605) will be visible by the amount of area (607) on the optical substrate (103) no longer covered by the wedge coating (655) leading to an indication of the amount removed over time. As this sliver is an indication of the thickness corroded (which is generally much smaller than the maximum thickness of the wedge coating (655)), the corrosion history can be monitored over a longer period of time, or under highly corrosive conditions, without the need to replace the window (450) as quickly. In particular, the wedge coating (650) described above should still be useable through about a mil of corrosion.

Figure 7:
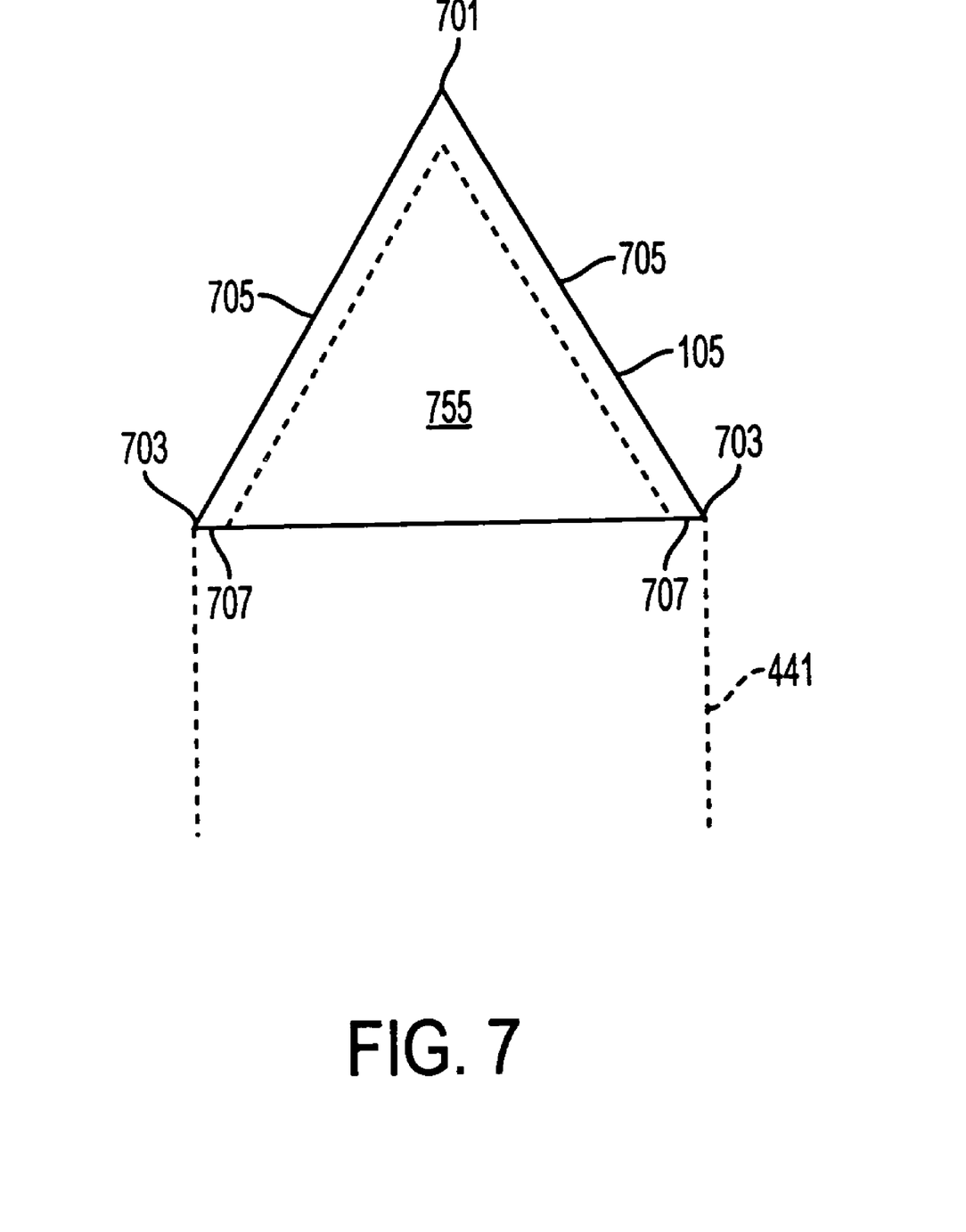
FIG. 7 provides a detail diagram showing an embodiment of an optical corrosion probe window with a cone coating.

A cone coating (755) is shown in FIG. 7. The cone coating (755) is also preferably about 3500 nm at the tip (701) of the cone and tapers off to about 0 nm at its widest circumference (703). Here the corrosion generally occurs uniformly around the edges until the center of the cone coating (755) is completely corroded and the percent reflectivity is zero. This method, therefore, works similar to the wedge coating (655), but can provide for a larger surface area of corrosion as the entire surface (705) of the cone is used compared to the flat surface (605) of the wedge coating (655) allowing for a greater area of material to be removed at the interface (707). Therefore the cone is effectively a design between the flat coating (555) and the wedge coating (655).

In a still further embodiment, particular shapes may be selected not because of their ability to measure general corrosion, but because of a shapes ability to particularly measure corrosion at a point of concern. For instance, the shape of the coating (105) may be chosen to simulate the design of a hairline fracture in the pipe. At such a fracture, corrosion may be of particular concern as the pipe already includes a point of weakness. This shape may therefore help to approximate how much corrosion, and even the nature of the corrosion, that is occurring at such a point. This may help to predict the possibility of a particular type of failure.

In a preferred embodiment of the invention, the percent reflectivity of the coating (105) is independent of the process stream (107), and the probe (400) functions simply based on calibration of the material of the coating (105) and the corrosion of that material compared to expected corrosion of the vessel. In this way, similar vessels can use similar probes (400) without recalibration. For instance, an iron pipe carrying water and an iron pipe carrying crude oil may be measured using identical probes (400) with an iron coating (105) as differences in corrosion effects between the two will be detected independent of the process stream (107), because the sensor will detect the amount of the coating (105) (iron in both cases) which has corroded off and that coating (105) is directly related to the material whose corrosion, in the same process stream, is desired to be extrapolated.

In an embodiment, the optical probe (400), will generally be placed anywhere within or partially within the pipe or process stream (107) to detect general corrosion. In an alternative embodiment, the optical probe (400) may be placed to monitor at a location of particular relevance, such as a joint or a point where corrosion is known to occur at a more rapid rate. Generally, the probe (400) will not be placed entirely within the process stream (107), although it may be in an embodiment. Instead, the optical substrate (103) and coating (105) will be placed in contact with the process stream (107) and only as much of the probe (400) as necessary to insure sealing of the probe (400) to the vessel will be placed in contact with the process stream (107). In this way, the probe (400) is generally more protected from being corroded itself and corrosion is preferably focused on the optical substrate (103) and coating (105).

The probe (400) may be located in the vessel which houses the process stream (107) by insertion through a process compatible fitting, a variety of which are known to those of ordinary skill in the art. In an alternative embodiment, the probe (400) is placed using a custom adapted spool piece that allows the probe (400) to be inserted and withdrawn from the process stream (107) using standard control techniques. Any other method of placing the window (450) in contact with the process stream (107) can be used so long as the window (450) is accessible to an appropriate light source (201) and detector (209). A variety of configurations for specialty piping or storage system inserts compatible with optical sensing are known to those of ordinary skill in the art. In a preferred embodiment, the probe (400) is inserted using a Welker Retractable Probe Device as is known to one of ordinary skill in the art.

In the above described embodiments, the probe (400) is presumed to be detecting chemically caused corrosion. In another embodiment, the optical probe (400) can respond to microbiologically grown films or other biological organisms which induce corrosion, (Microbiologically Induced Corrosion (MIC)). A population of biological organisms or biofilm can form on the coating (105) in the same way they would form on the piping. As corrosion is induced by the microorganism, the change in the reflectivity of the coating (105) will again be detected. In this case, the biological film itself may be absorbing the light, instead of it passing into the process stream (107).

Still further, mechanical erosion of the material from the corrosion effect will also be detected. This was alluded to previously. In some cases, this mechanical erosion may be just as important as the corrosion and may also occur on non-corroded materials at a slower rate. For instance, the conversion of iron to iron oxide serves to weaken the structure of the material. Therefore as corrosion occurs, the material will develop holes from the corrosion and the break down of the iron structure, but also from the iron oxide being pulled away from the other iron by the passage of the process stream (107). The corrosion monitoring system (300) takes both effects of corrosion into account as the physical presence of the coating (105) in the process stream (107) will expose the corroded surface to the same mechanical forces as those present elsewhere in the piping.

In the above described embodiments, it has been presumed that the coating (105) reflects the light. While this is the most common and easiest utilized phenomena in this type of detector, it is not necessarily the only one which may be used. In an alternative embodiment, the light need not be reflected by the coating (105) but may be absorbed and newly emitted. For instance, phosphorescent substances generally emit a particular light intensity based on their absorption of a particular light intensity of a different wavelength. In an embodiment, the coating (105) may allow for incident light to be absorbed and remitted at a different wavelength. Again as the coating (105) corrodes, the light intensity of the newly emitted light will be decreased as light incident on the coating (105) is decreased and more escapes into the process stream (107). In a still further embodiment, the coating (105) may refract or bend the light in a particular way, but may not reflect it. In this case, the detector (209) may be moved to a point where the refracted light is expected to be, or an additional reflective surface not exposed to the process stream (107) may reflect the refracted light back to the detector (209). Again, light which passes into the process stream (107) is not refracted and the decrease in the intensity of incident light can be used in detection.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A corrosion monitoring system comprising:
    a source of electromagnetic radiation;
    a detector of electromagnetic radiation; and
    a window comprising:
        an optical substrate; and
        a coating;
    wherein, said coating is placed in contact with a process stream that causes said coating to corrode over time;
    wherein, said source emits electromagnetic radiation through said optical substrate, at least a portion of said electromagnetic radiation reflecting from said coating;
    wherein said detector detects said reflected electromagnetic radiation; and
    wherein a level of corrosion of said coating can be extrapolated from the output of said detector.

2. The corrosion monitoring system of claim 1 wherein said optical substrate is selected from the group consisting of: sapphire, quartz, silica, glass, and plastic.

3. The corrosion monitoring system of claim 1 wherein said coating comprises a material used in a vessel housing said process stream.

4. The corrosion monitoring system of claim 3 wherein said coating comprises a material used in a tank.

5. The corrosion monitoring system of claim 3 wherein said coating comprises a material used in piping.

6. The corrosion monitoring system of claim 1 wherein said window is mounted in a probe and said source and said detector are in a processing system located remote from said probe.

7. The corrosion monitoring system of claim 6 wherein said probe is connected to said processing system via at least one fiber optic cable.

8. The corrosion monitoring system of claim 1 wherein said process stream includes crude oil.

9. The corrosion monitoring system of claim 1 wherein said process stream includes water.

10. The corrosion monitoring system of claim 1 wherein said process stream includes materials suspended therein.

11. The corrosion monitoring system of claim 1 wherein said electromagnetic radiation comprises visible light.

12. The corrosion monitoring system of claim 1 wherein said electromagnetic radiation comprises ultraviolet (UV) light.

13. The corrosion monitoring system of claim 1 wherein said electromagnetic radiation comprises infrared (IR) light.

14. A corrosion monitoring system comprising:
    an original intensity of electromagnetic radiation; and
    a window comprising:
        an optical substrate; and
        a coating which includes a material and a product of said material created by corrosion;
    wherein, said original intensity of electromagnetic radiation passes through said substrate and reflects from said coating, the electromagnetic radiation reflection from said coating having a lower intensity than the electromagnetic radiation reflection from said material alone; and
    wherein the ratio of said intensity of said electromagnetic radiation reflection from said coating to said intensity of said electromagnetic radiation reflection from said material is related to the ratio of said material to said product of said material created by corrosion.

15. The corrosion monitoring system of claim 14 wherein said electromagnetic radiation comprises visible light.

16. The corrosion monitoring system of claim 14 wherein said electromagnetic radiation comprises ultraviolet (UV) light.

17. The corrosion monitoring system of claim 14 wherein said electromagnetic radiation comprises infrared (IR) light.

18. A method for extrapolating the corrosion caused by a process stream, the method comprising:
    providing a probe including a window, said window including an optical substrate with a coating thereon;
    placing said probe in a manner such that said coating is in said process stream;
    illuminating said coating through said optical substrate with a first intensity of electromagnetic radiation, such that a first reflected intensity of said first intensity of electromagnetic radiation is specularly reflected by said coating;
    allowing said coating to be corroded by said process stream to create a corroded coating;
    illuminating said corroded coating through said optical substrate with said first intensity of electromagnetic radiation, such that a second reflected intensity of said first intensity of electromagnetic radiation is specularly reflected by said coating;
    comparing said first reflected intensity to said second reflected intensity; and
    extrapolating from said comparison the corrosion caused by said process stream.

19. The method of claim 18 wherein said intensity of electromagnetic radiation is the same in both said steps of illuminating.

20. The corrosion monitoring system of claim 18 wherein said electromagnetic radiation comprises visible light.

21. The corrosion monitoring system of claim 18 wherein said electromagnetic radiation comprises ultraviolet (UV) light.

22. The corrosion monitoring system of claim 18 wherein said electromagnetic radiation comprises infrared (IR) light.

* * * * *